United States Patent [19]

von Zeppelin et al.

[11] 4,248,233

[45] Feb. 3, 1981

[54] FORCEPS

[76] Inventors: Dieter von Zeppelin, Goethestrasse 30, 723 Schramberg 1; Wolfgang Sipli, Kapuzinerstrasse 36, 86 Bamberg 3, both of Fed. Rep. of Germany

[21] Appl. No.: 31,736

[22] Filed: Apr. 20, 1979

Related U.S. Application Data

[60] Division of Ser. No. 852,334, Nov. 17, 1977, Pat. No. 4,151,846, which is a continuation of Ser. No. 631,820, Nov. 14, 1975, abandoned.

[30] Foreign Application Priority Data

| Nov. 19, 1974 [DE] | Fed. Rep. of Germany | 2454762 |
| Dec. 18, 1974 [DE] | Fed. Rep. of Germany | 2459829 |
| Mar. 1, 1975 [DE] | Fed. Rep. of Germany | 2509009 |

[51] Int. Cl.$^3$ .................................. A61B 17/44
[52] U.S. Cl. ................................. 128/323; 81/318
[58] Field of Search ................ 128/321–325, 128/346, 354, 361; 81/341, 329, 331, 333, 302, 318, 319; 433/4, 159; 294/16, 28; 24/251, 260

[56] References Cited

U.S. PATENT DOCUMENTS

| 647,463 | 4/1900 | Beck | 128/324 |
| 820,845 | 5/1906 | Barton | 128/323 |
| 893,464 | 7/1908 | Dewees | 128/323 |
| 1,033,627 | 7/1912 | Sklar | 128/323 |
| 1,090,010 | 3/1914 | Armstrong et al. | 128/324 |
| 2,733,716 | 2/1956 | Roberts | 128/321 |
| 2,760,390 | 8/1956 | Ayer | 81/341 X |
| 2,863,158 | 12/1958 | Miller | 81/341 X |
| 3,271,847 | 9/1966 | Millheiser | 81/341 X |
| 3,384,088 | 5/1968 | Miseo | 128/323 |
| 3,550,595 | 12/1970 | Laufe | 128/323 |
| 3,681,840 | 8/1972 | Pool | 81/302 X |

FOREIGN PATENT DOCUMENTS

| 557538 | 5/1958 | Canada | 128/323 |
| 190106 | 4/1888 | France | 128/323 |

*Primary Examiner*—Robert W. Michell
*Assistant Examiner*—Michael H. Thaler
*Attorney, Agent, or Firm*—Kenway & Jenney

[57] ABSTRACT

Forceps characterized by leg-carried, separation distance controlling, devices which may be selectively manipulated.

2 Claims, 8 Drawing Figures

U.S. Patent    Feb. 3, 1981    Sheet 1 of 2    4,248,233
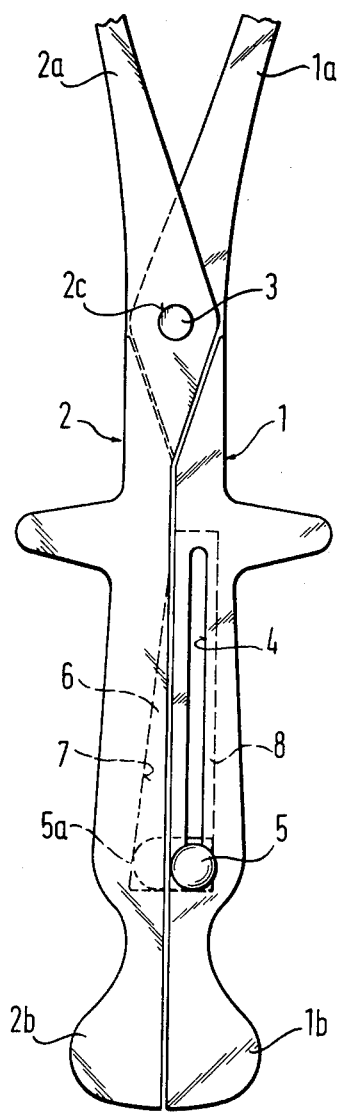
FIG. 1
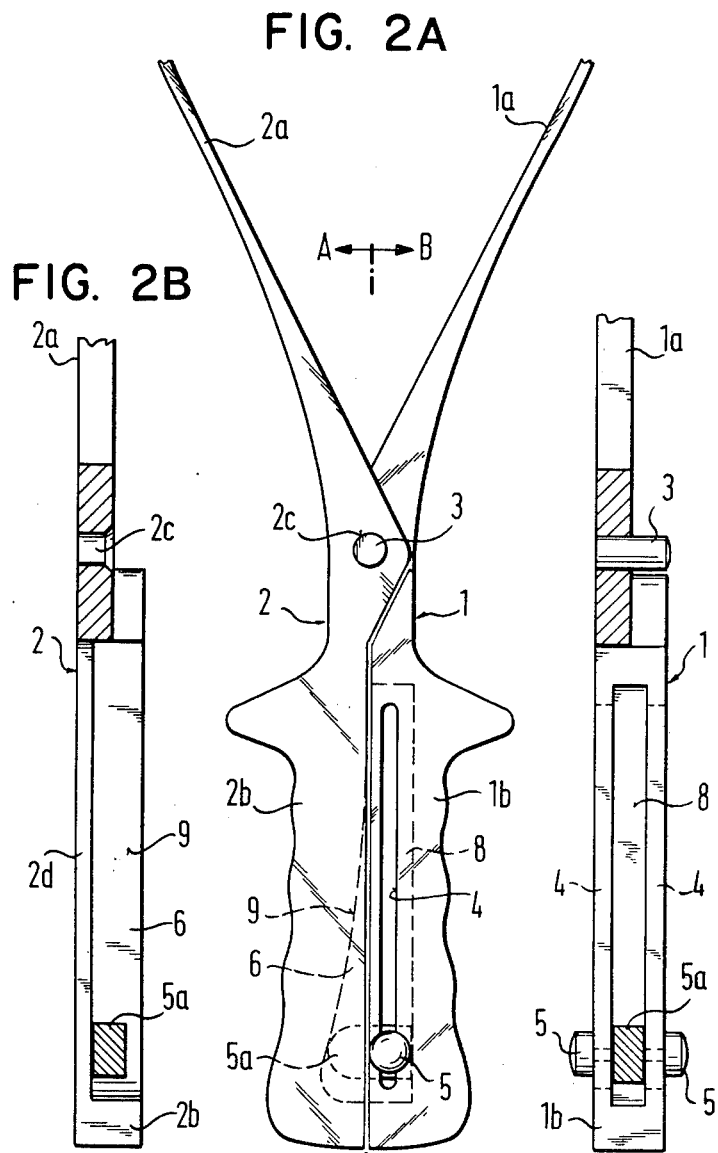
FIG. 2A
FIG. 2B
FIG. 2C
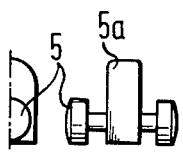
FIG. 2D

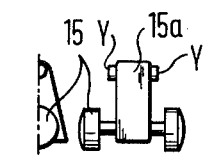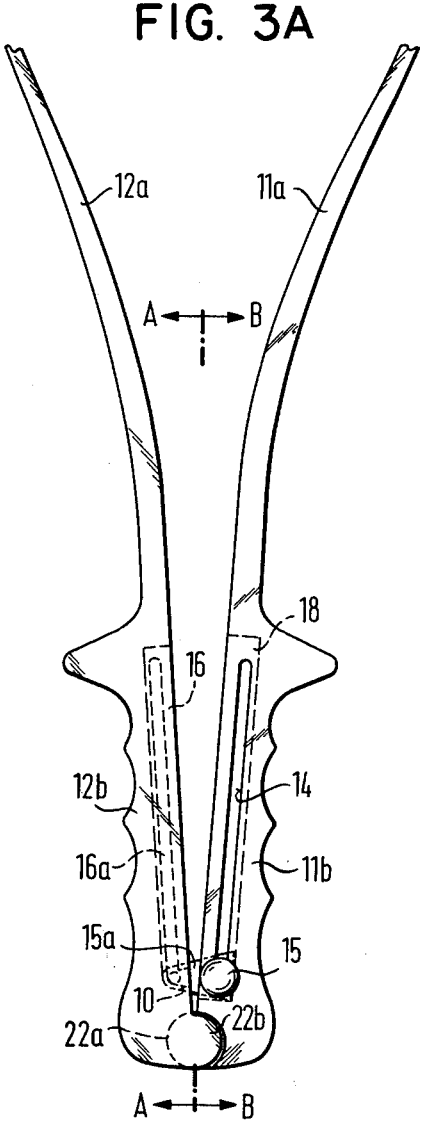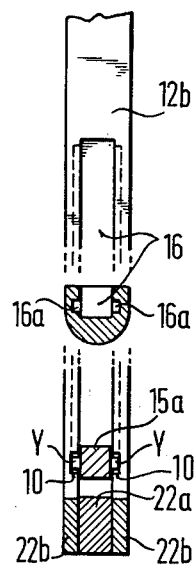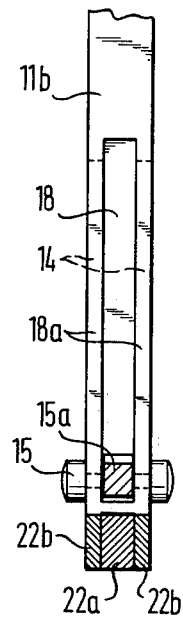
FIG. 3A
FIG. 3D
FIG. 3C
FIG. 3B

FORCEPS

This is a division of application Ser. No. 852,334, filed Nov. 17, 1977, now U.S. Pat. No. 4,151,846 which is a continuation of application Ser. No. 631,820 filed Nov. 14, 1975, now abandoned.

GENERAL BACKGROUND AND SUMMARY OF INVENTION

The invention relates to a forceps consisting of two tong parts which do not cross one another. Each tong part includes a tong spoon or head engaging portion and a tong leg. The leg is developed as handle. In addition, the tong legs are equipped with hinge members to provide an articulated interconnection.

A forceps of this general type is known in which the two tongs parts are equipped at their free ends with hinge members which render possible a releasable hinged connection of the two tong parts with each other. With such devices, the tong spoons are released when the tong legs are being gripped and the head of a child is being seized. In practice, it is extremely difficult to accurately determine the force acting on the head of the child since this is influenced by the pull exerted on the forceps. Thus, when this and other types of forceps are used, there frequently arise deformation injuries at the head of the child.

An object of this invention is to provide a forceps of the named kind, but wherein the pressure acting on the child can be effectively limited.

This objective is achieved by the invention through the inclusion, in the two tong legs, of a device that fixes the separation distance between the two tong spoons. The hinge members may be arranged between tong spoon and tong leg portions with the distance fixing device comprising a detent which braces the tong legs against one another. The hinge members may also be arranged at the free ends of the tong legs, with the fixing device being a part that lockingly engages each of the tong legs. Additional features of the invention follow from the attached disclosure. The forceps according to the invention is of simple construction, and easy and safe to operate. The forceps may also be easily cleaned.

DRAWINGS

The invention is explained hereunder, with reference to the drawings. In the drawings:

FIG. 1 provides a plan view of a first exemplified embodiment of the forceps according to the invention, with portions only the tong spoons (conventional) being shown;

FIG. 2(a) provides a plan view of a modified form of the FIG. 1 forceps wherein a bracing surface, engaging a sliding separation distance controlling member, has a convex curvature;

FIG. 2(b) provides a fragmentary, partially sectioned view of FIG. 2(a), viewed in direction A—A of FIG. 2(a);

FIG. 2(c) provides a fragmentary, partially sectioned view of FIG. 2(a) as viewed along direction B—B of FIG. 2(a);

FIG. 2(d) provides an elevational and end view of a separation distance controlling device incorporated in the FIG. 2(a) forceps.

FIG. 3(a) provides a plan view of still another modified embodiment of the forceps according to the invention;

FIG. 3(b) provides a fragmentary, partially sectioned view of FIG. 3(a) as viewed along direction A—A of FIG. 3(a);

FIG. 3(c) provides a fragmentary, partially sectioned view of FIG. 3(a) as viewed along direction B—B of FIG. 3(a); and FIG. 3(d) provides an elevational and end view of a separation distance controlling member included in the FIG. 3(a) device.

DETAILED DESCRIPTION

The forceps represented in FIGS. 1 and 2 consist of the two tong parts 1 and 2. These parts have tong spoons 1a and 2a, respectively, and tong legs 1b and 2b, respectively.

The tong part 1 is provided with a hinge pin 3, while the tong part 2 has a hole 2c for removably receiving the pin 3. In this way the tong parts 1 and 2 can be articulatedly connected with each other in a simple manner, through the joining of pin and hole, and readily separated for cleaning purposes.

The two tong parts do not cross one another (in the sense that sissors parts cross) so that in the position shown in FIGS. 1 and 2, i.e., when the tong legs or handles 1b, 2b are directly mating, the tong spoons 1a, 2a display the widest opening, and are moved toward one another when the tong legs are moved apart.

In practice, there is first inserted the right tong spoon and then the left one, these parts are laid against the head of the child, and the parts are then articulatedly interconnected. Thereupon a limiting device 5, 5a is so adjusted that the two tong legs are braced against one another. When now the tong legs are gripped with the hand, the pressure of the tong spoons at the head of the child cannot be further changed. On the other hand, an adjustment of the limiting device assures, in a simple manner, a quick opening of the forceps.

The limiting device is represented in the drawing as a sliding member which consists of a detent or bracing part 5a and a handle 5. The detect part 5a is guided in a groove 8 in tong leg 1b. The boundary walls of this groove are provided with a slot 4 through which the handle 5 projects.

A flat base of the detent 5a slides along the flat outer base wall of groove 8, with this generally conforming, slideable engagement being maintained by the alignment of the handle 5 in slot means 4, as shown in FIGS. 1 and 4. The outer end of detent 5a, which may be curved as shown, projects into a groove 6 in part 2. This outer end is operable to bracingly engage a groove base or bottom wall 7, extending generally longitudinally of the forceps but sloping inwardly, as shown in FIG. 1. As shown, wall 7 may comprise an inclined plane.

As is readily evident, the forceps parts may be mutually braced and immobilized relative to each other by means of the slideable limiting device 5, 5a. This device may be readily manipulated into any arbitrary position along wall 7. Whenever a force is exerted upon the tong spoons tending to separate the spoons, which may occur, e.g., through engagement with the head of a child seized by the forceps, the detent 5a may be positioned so that a converging force exerted on the detent braced legs will be exerted so as to limit separation of the properly positioned spoons. This provides a safety factor in that the detent controls spoon separation, rather than convergence.

The embodiment according to FIG. 2a is like that of FIG. 1 but differs from that of FIG. 1 essentially in that the bottom of the groove 6, which engages the free end of the detent part, is curved. This curvature, as shown in FIG. 2a, is preferably concave, by means of which there can be achieved, for example, an opening of the forceps which is linearly dependent on the position of the sliding member 5, 5a along groove 4 and where the angle between the detent part and concavely curved groove base wall remains generally constant. Through this arrangement there results a linear, i.e. directly proportional relationship between the position of the sliding member 5, 5a and the separation distance between the tong spoons.

To render it possible to introduce the free end of detent 5a into the groove 6, even when the forceps is fully opened as shown in FIG. 1, there may be provided an opening in a side wall of groove 6. This opening could be adapted to the dimension of detent 5a so that the detent 5a could be laterally passed through the opening when the forceps parts were assembled in the FIG. 1 "open" condition.

However, it is also possible to completely omit such a side wall as is shown in FIG. 2b. Here the groove 6, with curved bottom or base 9 is laterally limited by only one side wall 2d so that the tong parts may be laterally interconnected in any arbitrary position of the sliding member 5,5a.

The illustrated sliding member has proven to be particularly beneficial as a limiting device. But in principle it is also possible to use a differently constructed limiting device. For example, this device may take the form of an eccentric disc arranged at one tong leg, or the form of a set screw passing through one tong leg, or also the form of a pressure cylinder—arranged in one tong leg—whose piston is braced against the other tong leg.

In the embodiment according to FIG. 3a, the tong spoons are denoted by 11a, 12a and the tong legs by 11b, 12b. At the free ends of legs there are provided arcuate, tongue and groove bearing or pivot members 22a and 22b, which are mutually telescopable to define a pivot joint.

The sliding detent or separation distance controlling member 15/15a of this embodiment glides in a mounting groove 18 in the tong leg 11b and is secured by elongated slots 14 of the groove walls 18a which receive recessed portions of handle 15.

In the tong leg 12b there is provided a groove 16 with lateral widenings or recesses 16a. The bracing projection 15a of sliding member 15 includes pin projection or lateral studs Y which project into grooves 16a and are slideable therealong. This provides an interlocking connection between sliding member 15/15a and tong leg 12b and an interlocking connection between the two tong legs 11b and 12b.

To permit insertion of the projection 15a and its studs Y, into groove 16 with its wall recesses 16a, there are provided at one end of groove 16, openings 10 in the side walls of groove 16 (see FIG. 2b). When the sliding member 15 in slid in a direction toward the tong spoons 11a, 12a, after this insertion, the studs Y engage in the lateral widenings 16a. This accomplishes an interlocking connection between the tong legs 11b, 12b.

When the sliding member or detent handle 15 is slid in a direction toward the tong spoons (after the above noted interlocking is effected), these spoons are automatically brought closer together. Thus, in dependence on the position of sliding member 15, a desired and controlled forceps opening can be achieved, with the tong spoons being interlocked with each other through the sliding member 15 so that the forceps can neither be opened up more nor closed any further.

A complete opening of the forceps and a taking apart of the two tong parts is possible when the sliding member 15 is in its end position as shown in FIG. 3a.

As will be now recognized, through the use of appropriate openings in the base portions of the side walls of grooves 8 and 18, the detent members 5/5a and 15/15a may be made selectively separable from the forceps parts 1a and 11a, respectively. Such openings may be akin in function to the openings 10, above noted.

SUMMARY OF ADVANTAGES AND SCOPE OF INVENTION

The present invention provides a particular advantage in affording a forceps where the spoon (i.e. head engaging portion) separation may be positively controlled and braced. This tends to minimize and/or eliminate forceps damage caused by the exertion of improper force on a baby's head during delivery.

Moreover, the separable nature of the forceps elements readily permits sanitizing and cleaning operations.

Those skilled in the art and familiar with this disclosure will appreciate that additions, deletions, substitutions and other modifications may be made within the scope of the invention as set forth in the appended claims.

What is claimed is:

1. Obstetrical forceps comprising:

two non-crossing tong parts, each said part having a baby head engaging tong spoon, and a tong leg providing a handle disposed to be gripped by a user's hand; said handles being mutually engageable to define the minimum distance between said tong spoons;

manually engageable and disengageable hinge means operable to hingedly connect said legs of said two parts, comprising a first member carried by one of said tong legs, and a second member carried by the other of said tong legs, said members being adapted to telescopically engage one another, said hinge means being located at the ends of said tong legs remote from said tong spoons; and bracing means received in a mounting groove in one of said leg handles for longitudinal movement with respect to said tong leg handle, said bracing means including a portion disposed between said tong parts to be engageable with a surface of the other tong leg handle and a portion exposed for engagement by a user's hand gripping said leg handles, said bracing means thereby operable to adjustably fix a minimum distance between the tong legs, and thus the tong spoons of said two tong parts, said bracing means being moveable generally away from said hinge means to effect relative closure of said tong spoons;

the other of said legs defining an interlocking groove, said bracing means including retaining means for engaging said interlocking groove, whereby said tong parts facilitate manual hinge means engagement and tong spoon separation adjustment without the user removing his hands from said handles after insertion of the tong spoons into a body cavity.

2. A medical forceps according to claim 1 wherein the other of said legs defines an opening communicating with said interlocking groove, by which said bracing retaining means may engage said interlocking groove, wherein said opening is located at an end of said interlocking groove adjacent said hinge means.

* * * * *